(12) United States Patent
Omori et al.

(10) Patent No.: US 6,605,733 B2
(45) Date of Patent: Aug. 12, 2003

(54) TITANIUM-CONTAINING SOLID CATALYST AND PROCESS FOR PRODUCING EPOXY COMPOUND USING THE SAME

(75) Inventors: Hideki Omori, Ichihara (JP); Hiroko Ahara, Ichihara (JP); Kazuhiko Haba, Ichihara (JP); Yoshiaki Takaya, Ichihara (JP); Shin Irie, Funabashi (JP)

(73) Assignee: Maruzen Petrochemical Co., Ltd., Tokyo (JP)

( * ) Notice: Subject to any disclaimer, the term of this patent is extended or adjusted under 35 U.S.C. 154(b) by 49 days.

(21) Appl. No.: 10/028,785

(22) Filed: Dec. 28, 2001

(65) Prior Publication Data

US 2002/0137956 A1 Sep. 26, 2002

(30) Foreign Application Priority Data

Jan. 15, 2001 (JP) ........................................ 2001-006318
Apr. 20, 2001 (JP) ........................................ 2001-122967

(51) Int. Cl.[7] ................... C07D 301/12; C07D 301/19; B01J 21/08
(52) U.S. Cl. ...................... 549/529; 549/523; 549/524; 549/531; 502/242
(58) Field of Search ................ 549/523, 524, 549/529, 531; 502/242

(56) References Cited

U.S. PATENT DOCUMENTS 4,176,089 A * 11/1979 Cull ........................... 502/236
5,840,650 A * 11/1998 Tamura et al. .............. 502/350
6,355,596 B2 * 3/2002 Hu et al. ..................... 502/350

FOREIGN PATENT DOCUMENTS

| GB | 1249079 | * 10/1971 |
| GB | 1332526 | * 10/1973 |
| GB | 1339309 | * 12/1973 |
| JP | 50-30049 | 9/1975 |
| JP | 54-40525 | 12/1979 |
| JP | 54-40526 | 12/1979 |
| JP | 56-35491 | 8/1981 |
| JP | 8-269031 | 10/1996 |

OTHER PUBLICATIONS

M. C. Capel–Sanchez, et al., Chem. Commun., pp. 855–856, "Effective Alkene Epoxidation with Dilute Hydrogen Peroxide on Amorphous Silica–Supported Titanium Catalysts", 2000.

* cited by examiner

Primary Examiner—Flona T. Powers
(74) Attorney, Agent, or Firm—Oblon, Spivak, McClelland, Maier & Neustadt, P.C.

(57) ABSTRACT

Provided are a titanium-containing solid catalyst useful for producing an epoxy compound from an olefin compound and a peroxide, and a process for producing an epoxy compound using said catalyst.

The titanium-containing solid catalyst is obtainable by calcination of a titanium alkynyl alkoxide supported on a silica gel.

12 Claims, 2 Drawing Sheets

US 6,605,733 B2

TITANIUM-CONTAINING SOLID CATALYST AND PROCESS FOR PRODUCING EPOXY COMPOUND USING THE SAME

TECHNICAL FIELD

The present invention relates to a titanium-containing solid catalyst useful for production of epoxy compounds and a process for producing epoxy compounds by using the catalyst.

BACKGROUND ART

As a process for producing an epoxy compound by reacting an olefin compound with a peroxide in the presence of a titanium-containing solid catalyst, several processes are conventionally known, for example, those described in JP-B-50-30049, JP-B-54-40525, JP-B-54-40526, JP-B-56-35491 and JP-A-8-269031.

The above-described titanium-containing solid catalyst can be prepared in various processes. Among them, useful is a process of calcining the titanium compound which has been impregnated into a silica gel carrier in a solvent. As the titanium compound, titanium saturated alkoxides are employed most frequently. Conversion of a titanium alkoxide into titanium oxide when it is supported on a carrier, however, prevents the solid catalyst thus prepared from exhibiting catalytic activity in an epoxidation reaction.

In general, use of highly dispersed titanium having a tetrahedral structure is necessary for production of a titanium-containing solid catalyst capable of exhibiting a high activity in an epoxidation reaction. For producing such catalyst containing highly dispersed titanium, a stable titanium alkoxide must be prepared by suppressing generation of clusters of titanium oxide or titanium during preparation of the catalyst.

For preparing the above-described catalyst, use of a bulky saturated alcohol, for example, cyclohexanol (Chem. Commun. 2000, 855) is generally known. To achieve a higher activity in an epoxidation reaction, preparation of more stable titanium alkoxide is required.

An object of the present invention is to provide a titanium-containing solid catalyst having a high activity and a high epoxy selectivity by overcoming the above-described problems involved in the titanium alkoxide preparation for improving the activity of the catalyst in the production of an epoxy compound (oxysilane compound), and also to provide a process for producing epoxy compounds using this catalyst.

DISCLOSURE OF THE INVENTION

In order to attaining the above-described object, the present inventors have carried out an extensive investigation. As a result, it has been found that when an alkynyl alcohol is used for preparation of a titanium alkoxide from a titanium compound raw material, a titanium alkynyl alkoxide can be prepared readily; that the titanium alkynyl alkoxide supported on silica gel is stable; and that a catalyst obtainable by calcining a titanium alkynyl alkoxide supported on a silica gel has a high activity and a high epoxy selectivity, to complete the invention.

In the present invention, there is thus provided a titanium-containing solid catalyst obtainable by calcining a titanium alkynyl alkoxide supported on a silica gel.

In the present invention, there is also provided a process for producing an epoxy compound, which comprises reacting an olefin compound with a peroxide in the presence of the above-described titanium-containing solid catalyst.

BEST MODE FOR CARRYING OUT THE INVENTION

The titanium-containing solid catalyst of the present invention can be obtained by calcining the titanium alkynyl alkoxide supported on a silica gel. The titanium alkynyl alkoxide is a titanium (IV) alkynyl alkoxide. A silica gel carrying a titanium alkynyl alkoxide may be obtained by supporting a titanium alkynyl alkoxide, which has been prepared in advance, on silica gel, but is effectively produced by supporting a titanium compound on silica gel by using an alkynyl alcohol and then forming the corresponding titanium alkynyl alkoxide in the reaction mixture. More specifically, the titanium compound can be supported on silica gel in the presence of an alkynyl alcohol. This supporting reaction can be usually conducted at room temperature. The titanium alkynyl alkoxide varies depending on the titanium compound raw material and alkynyl alcohol which are hereinafter described and includes titanium alkynyl alkoxides having $C_3$ to $C_{16}$ alkynyl groups such as titanium propargyl alkoxide and titanium (1-butin-3-alkoxide).

Examples of the titanium compound raw material used for preparation of the above-described titanium alkynyl alkoxide include titanium saturated alkoxides such as titanium methoxide, titanium ethoxide, titanium propoxide, titanium isopropoxide, titanium butoxide and titanium isobutoxide; and titanium dialkoxydialkanatos such as titanium diisopropoxide bis(acetyl-acetonato), with titanium di($C_{1-6}$ alkoxy)-di($C_{1-6}$ alkanatos) being preferred.

Alkynyl alcohols can be aliphatic alcohols having one or more carbon-carbon triple bonds, with $C_{3-16}$ aliphatic alcohols having one carbon-carbon triple bond being preferred. As the alkynyl alcohols, 3-alkynyl alcohols such as propargyl alcohol, 3,5-dimethyl-1-hexyn-3-ol, 2-butyn-1,4-diol and 1-butyn-3-ol are more preferred, with $C_{3-16}$ 3-alkynyl alcohols being still more preferred and propargyl alcohol being particularly preferred.

Figure 1:
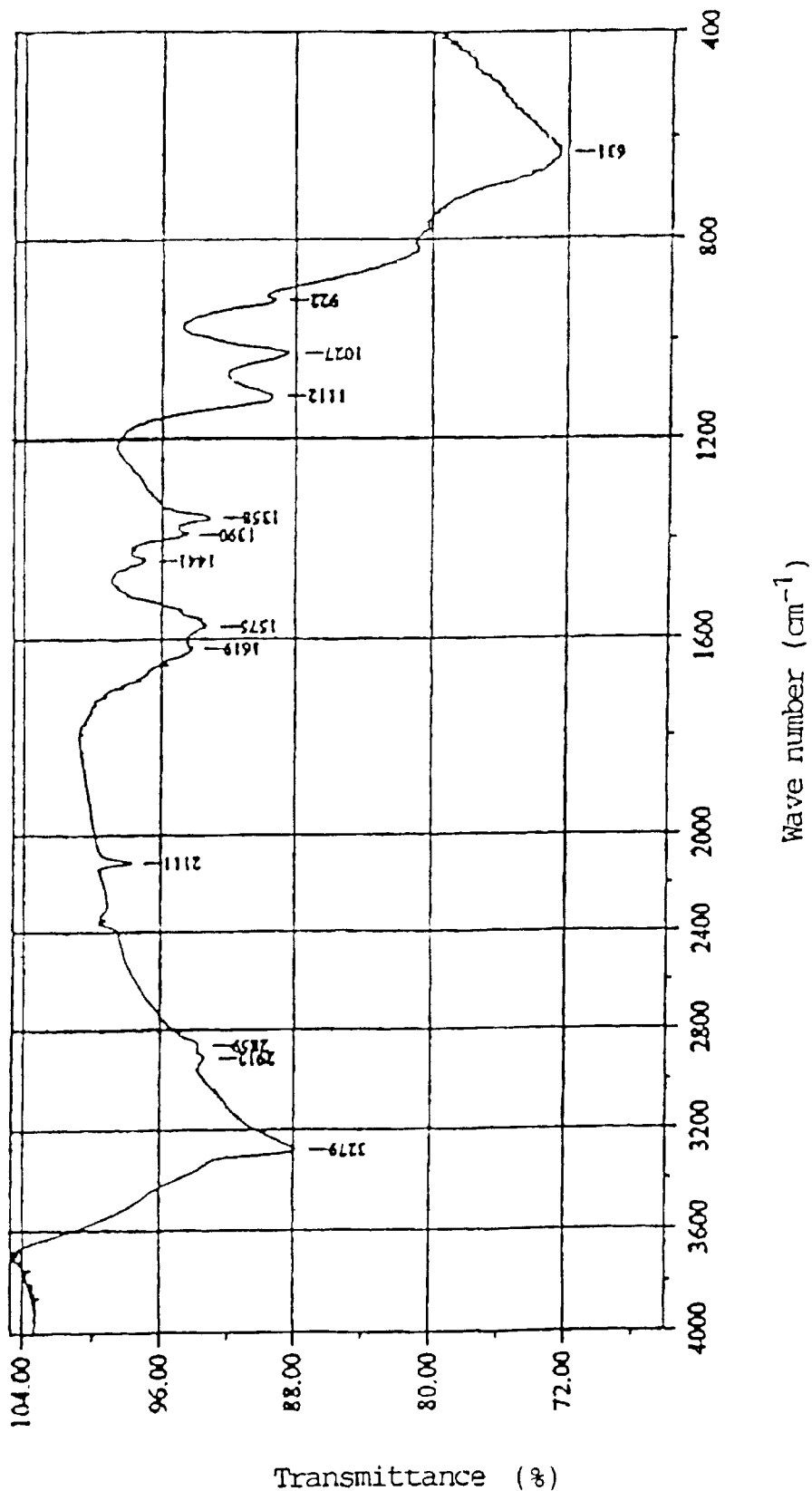
FIG. 1 illustrates an IR spectrum of the product obtained by reacting titanium tetraisopropoxide with propargyl alcohol at room temperature in the presence of silica gel.
Figure 2:
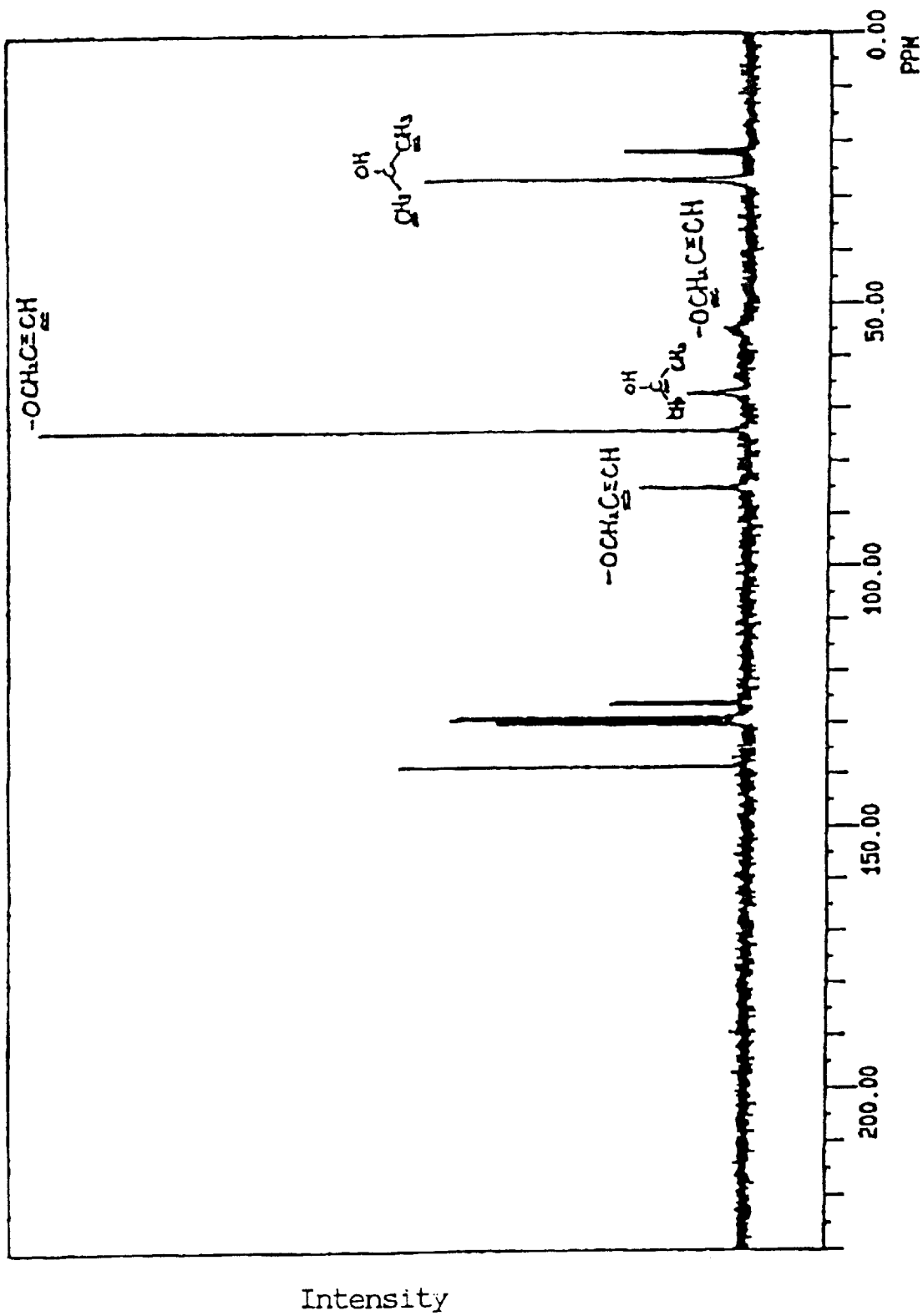
FIG. 2 illustrates a $^{13}$C-NMR spectrum of the product obtained by reacting titanium tetraisopropoxide with propargyl alcohol at room temperature.

The alkynyl alcohol is preferably used in an amount of 4 moles or more, if possible 4 to 10 moles, per mole of the titanium compound. The reaction is usually effected at room temperature, preferably within a range of from room temperature to 90° C. The reaction time is usually about 20 minutes to 1 hour. Any of the above-mentioned titanium compounds causes alcohol exchange readily in an alkynyl alcohol, thereby forming the corresponding titanium alkynyl alkoxide. For example, when titanium isopropoxide is employed as the titanium compound, exchange reaction with propargyl alcohol occurs readily at room temperature, followed by formation of the corresponding titanium propargyl alkoxide and dissociation of isopropyl alcohol. Formation of the titanium propargyl alkoxide and dissociation of isopropyl alcohol were confirmed by the NMR (FIG. 2), and incorporation of a carbon-carbon triple bond in the resulting titanium propargyl alkoxide supported on silica gel was confirmed by the IR spectrum (FIG. 1).

The titanium alkynyl alkoxide thus formed is markedly stable even in the air, suggesting a firm bonding of the alkynylalkoxy group to titanium. This stability is presumed to result from a strong or firm coordination of the alkynylalkoxy group to titanium due to the resonance stabilization of the alkynylalkoxy group.

The silica gel-supported titanium alkynyl alkoxide thus obtained can be calcined sufficiently at 400 to 900° C., preferably at 400 to 600° C. Calcination time ranges from 1 to 18 hours, with 4 to 6 hours being preferred.

In the titanium-containing solid catalyst of the present invention thus obtained, titanium is highly dispersed on silica gel. The silica/titanium ratio (molar ratio) of the catalyst is preferably 40/1 to 500/1 in view of compatible attainment of catalytic activity and epoxy selectivity. The silica/titanium ratio in the titanium-containing solid catalyst can be measured by means of fluorescent X-rays. A sample for the measurement can be prepared by a molten bead method. This silica/titanium ratio indicates the degree of dispersion of titanium in silica gel. A smaller value indicates a higher degree of dispersion.

The titanium-containing solid catalyst thus obtained is especially useful as a catalyst for producing an epoxy compound by reacting an olefin compound with a peroxide.

The olefin compound to be used in the present invention can be non-cyclic, monocyclic, dicyclic or polycyclic and at the same time, can be a monoolefin, diolefin or polyolefin. When the olefin compound contains at least two olefinic bonds, they may be a conjugated bond or non-conjugated bond. Mono- or diolefin compounds having 2 to 60 carbon atoms are usually preferred. Such olefin compounds include ethylene, propylene, butene-1, butene-2, isobutene, hexene-1, hexene-2, hexene-3, octene-1, decene-1, styrene, cyclopentene, cyclohexene, cyclooctene, butadiene, isoprene, cyclopentadiene, dicyclopentadiene and vinylcyclohexene.

For the epoxidation, an organic hydroperoxide or hydrogen peroxide can be used as the peroxide. Organic hydroperoxides include tert-butyl hydroperoxide, ethylbenzene hydroperoxide, cyclopentane hydroperoxide and cyclohexane hydroperoxide. A solution of such peroxide either in an organic solvent or water can be used for the epoxidation, with a decane solution of tert-butyl hydroperoxide being particularly preferred.

The epoxidation according to the present invention is effected by using a peroxide in an amount not less than the moles of the olefinic double bond in the olefin compound. Preferably, the peroxide is used in an amount of 1 to 1.5 moles per mole of the olefinic double bond. The epoxidation is usually conducted at 10 to 140° C., preferably 60 to 100° C. As a reaction solvent, alkanes such as hexane, octane and decane, ethers such as diethyl ether and dibutyl ether, and alcohols such as isopropyl alcohol and tert-butyl alcohol can be employed, with tert-butyl alcohol being especially preferred.

The epoxidation according to the present invention can be conducted advantageously by using the titanium-containing solid catalyst of the present invention in the form of a slurry or fixed bed. The raw materials are supplied at LHSV (Liquid Hourly Space Velocity) of 0.01 to 10/h. The solid bed is suited for a large-scale industrial operation. The process of the present invention can be carried out by a batch, semi-continuous or continuous system.

Epoxy compounds obtainable according to the epoxidation of the present invention are olefin oxides corresponding to the olefin compounds used as a raw material. Examples include ethylene oxide, propylene oxide, (1,2-) epoxyhexane, (1,2-)epoxyoctane, cyclohexane epoxide, 4-vinyl-1,2-epoxyhexane and cyclopentane epoxide.

After completion of the epoxidation, a liquid mixture containing the desired product is easily separable from the catalyst composition. Then, the liquid mixture can be purified in a proper manner. Purification includes fractional distillation, selective extraction, filtration and washing. The solvent, catalyst, unreacted olefin and unreacted peroxide can be recovered and recycled.

EXAMPLES

The present invention will be hereinafter described in further detail by way of examples. It should however be borne in mind that the present invention is by no means limited thereto or thereby.

Example 1

Preparation of a Titanium-containing Solid Catalyst

After a mixture of 1.06 g of titanium tetra-isopropoxide and 200 g of propargyl alcohol (PGA) was stirred at 80° C. for 30 minutes, 7 g of silica gel 100 (BET: 270 to 370 m$^2$/g, pore volume: 0.9 to 1.2 mL/g, particle size: 0.063 to 0.02 mm) was added. The resulting mixture was refluxed for 2 hours. After the reaction mixture was allowed to cool, it was filtered to collect the solid, followed by drying. The IR spectrum of the product thus obtained is shown in FIG. 1. The resulting product was calcined at 500° C. for 5 hours, whereby a titanium-containing solid catalyst having a silica/titanium ratio (molar ratio) of 46.0/1 was prepared.

Evaluation Method

The amount of the organic substance and the amount of the peroxide consumed were determined by the FID-GC method and iodometry, respectively.

Example 2

To 12.0 g of tert-butyl alcohol were added 0.5 g of the solid catalyst prepared in Example 1, 2.00 g (18.5 mmol) of vinylcyclohexene (VCH), 3.03 g (18.5 mmol) of a decane solution of tert-butyl hydroperoxide (TBHP). The mixture was reacted at 80° C. for 24 hours. The results are shown in Table 1.

Example 3

Under similar conditions to Example 2 except that 0.33 g (2.57 mmol) of an aqueous solution of tert-butyl hydroperoxide (TBHP aq) was used as the peroxide, the reaction was effected. The results are shown in Table 1.

Example 4

To 6.0 g of tert-butyl alcohol were added 0.25 g of the solid catalyst prepared in Example 1, 1.12 g (10.0 mmol) of octene-1 (OCT-1) and 0.16 g (1.00 mmol) of TBHP. The mixture was reacted at 80° C. for 24 hours. The results are shown in Table 1.

Example 5

Under similar conditions to Example 4 except that 1.08 g (1.00 mmol) of cyclopentene (CPE) was used instead of octene-1 as the olefin compound, the reaction was effected. The results are shown in Table 1.

Example 6

A titanium-containing solid catalyst was prepared in a similar manner to Example 1 except that 200 g of 3,5- dimethyl-1-hexyn-3-ol (PGA35) was used instead of propargyl alcohol. To 12.0 g of tert-butyl alcohol were added 0.5 g of the resulting solid catalyst, 2.00 g (18.5 mmol) of vinylcyclohexene (VCH) and 2.37 g (18.40 mmol) of TBHPaq, followed by reaction at 80° C. for 24 hours. The results are shown in Table 1. The conversion ratio of the peroxide and the epoxy selectivity were determined by iodometry and gas chromatography measurements, respectively.

TABLE 1

| Examples | 2 | 3 | 4 | 5 | 6 |
|---|---|---|---|---|---|
| Alcohol for preparation of catalyst | PGA | PGA | PGA | PGA | PGA35 |
| Olefin compound | VCH | VCH | OCT-1 | CPE | VCH |
| Peroxide | TBHP | TBHPaq | TBHP | TBHP | TBHPaq |
| Conversion ratio (%) of peroxide | 72.1 | 50.7 | 85.8 | 97.4 | 50.9 |
| Epoxy selectivity (%) | 90.0 | 91.8 | >99 | >99 | 80.0 |

PGA: propargyl alcohol
PGA35: 3,5-dimethyl-1-hexyn-3-ol
VCH: vinylcyclohexene
OCT-1: octene-1
CPE: cyclopentene
TBHP: decane solution of tert-butyl hydroperoxide
TBHPaq: aqueous solution of tert-butyl hydroperoxide Example 7

Preparation of Titanium-containing Solid Catalyst

In a similar manner to Example 1 except that the amount of silica gel 100 was changed to 14 g, a titanium-containing solid catalyst having a silica/titanium molar ratio of 84.0/1 was prepared.

Example 8

To 12.0 g of tert-butyl alcohol were added 0.5 g of the solid catalyst prepared in Example 7, 2.00 g (18.5 mmol) of vinylcyclohexene (VCH), 3.03 g (18.5 mmol) of a decane solution of tert-butyl hydroperoxide (TBHP), followed by reaction at 80° C. for 24 hours. The results are shown in Table 2.

Comparative Example 1

In a similar manner to Example 7 except that 200 g of toluene was used instead of PGA, a solid catalyst was prepared. To 12.0 g of tert-butyl alcohol were added 0.5 g of the resulting solid catalyst, 2.00 g of VCH and 2.37 g of TBHPaq, followed by reaction at 80° C. for 24 hours. The results are shown in Table 2. The conversion ratio of the peroxide and the epoxy selectivity were determined as in Table 1.

TABLE 2

| | Example 8 | Comparative Example 1 |
|---|---|---|
| Alcohol for preparation of catalyst | PGA | TOL |
| Olefin compound | VCH | VCH |
| Peroxide | TBHP | TBHPaq |

TABLE 2-continued

| | Example 8 | Comparative Example 1 |
|---|---|---|
| Conversion ratio (%) of peroxide | 81.8 | <1 |
| Epoxy selectivity (%) | 93.0 | 0 |

PGA: propargyl alcohol
VCH: vinylcyclcohexene
TOL: toluene
TBHP: decane solution of t-butyl hydroperoxide
TBHPaq: aqueous solution of t-butyl hydroperoxide Example 9

Investigation of the Life of the Catalyst Prepared in the Above

To 300.0 g of tert-butyl alcohol were added 10.50 g of the catalyst prepared in Example 1, 50.00 g (0.74 mol) of cyclopentene (CPE) and 121.00 g (0.74 mol) of a decane solution of TBHP, followed by reaction at 80° C. for 24 hours. After completion of the reaction, the catalyst was collected and dried. Reaction was repeated under similar conditions and the results are shown in Table 3.

TABLE 3

| | 1st | 2nd | 3rd | 4th | 5th |
|---|---|---|---|---|---|
| Conversion ratio (%) of peroxide | 69.7 | 68.0 | 61.3 | 61.3 | 61.4 |
| Epoxy selectivity (%) | >99 | >99 | >99 | >99 | >99 |

Example 10

Investigation of the Activity of the Resulting Catalyst in a Fixed Bed

A solution obtained by adding, to 55.0 g of tert-butyl alcohol, 27.92 (0.41 mol) of cyclopentene (CPE) and 26.87 a (0.16 mol) of a decane solution of TBHP was allowed to flow at 80° C. under normal pressure at LHSV (Liquid Hourly Space Velocity) of 1.0/h through the fixed bed of 2.00 g (5 cc) of the catalyst prepared in Example 1 and liquid flow reaction was effected. The results are shown in Table 4. The conversion ratio of the peroxide and the epoxy selectivity were determined as in Table 1.

TABLE 4

| | 2 hours | 5 hours | 9 hours |
|---|---|---|---|
| Conversion ratio (%) of peroxide | 61 | 60 | 60 |
| Epoxy selectivity (%) | 91 | 92 | 91 |

As is apparent from Tables 1 and 2, it was found that in any olefin compound and irrespective of whether the peroxide is in the form of a solution in an organic solvent or in water, the catalyst of the present invention can attain a high epoxy selectivity and a high conversion ratio of a peroxide. Since the unreacted peroxide exists in the reaction system without being decomposed, the conversion ratio can be improved further by prolongation of the reaction time.

In Table 3, the amount of the peroxide consumed remains constant at about 61% in the 3rd to 5th reactions, while selectivity is higher than 99% (>99%); no deterioration is recognized at all. These results suggest that the catalyst system of the invention can be repeatedly used for the reaction.

In Table 4, the amount of the peroxide consumed remains constant at about 60% irrespective of the reaction time, and the selectivity reaches 91% or more in any reaction time. These results suggest that the catalyst system of the present invention exhibits practical activity and selectivity in a fixed-bed liquid flow reaction.

INDUSTRIAL APPLICABILITY

By reacting an olefin compound with a peroxide in the presence of a titanium-containing solid catalyst which is obtainable by calcining a titanium alkynyl alkoxide supported on a silica gel, an epoxy compound can be obtained at a high conversion ratio from a peroxide and at a high epoxy selectivity. In addition, the solid catalyst of the present invention can be reused as it is.

What is claimed is:

1. A titanium-containing solid catalyst obtained by calcining a titanium alkynyl alkoxide supported on a silica gel.

2. The titanium-containing solid catalyst according to claim 1, wherein the titanium alkynyl alkoxide supported on a silica gel is obtained by supporting a titanium compound on a silica gel by using an alkynyl alcohol.

3. The titanium-containing solid catalyst according to claim 2, wherein the alkynyl alcohol is propargyl alcohol.

4. The titanium-containing solid catalyst according to claim 1, wherein the silica/titanium molar ratio of the catalyst is 40 to 500.

5. The titanium-containing solid catalyst according to claim 2, wherein the silica/titanium molar ratio of the catalyst is 40 to 500.

6. The titanium-containing solid catalyst according to claim 1, which is a catalyst for producing an epoxy compound by reacting an olefin compound with a peroxide.

7. A process for producing an epoxy compound, which comprises reacting an olefin compound with a peroxide in the presence of a titanium-containing solid catalyst obtained by calcining a titanium alkynyl alkoxide supported on a silica gel.

8. The process for producing an epoxy compound according to claim 7, wherein the titanium alkynyl alkoxide supported on a silica gel is obtained by supporting a titanium compound on a silica gel by using an alkynyl alcohol.

9. The process for producing an epoxy compound according to claim 8, wherein the alkynyl alcohol is propargyl alcohol.

10. The process for producing an epoxy compound according to claim 7, wherein the peroxide is tert-butyl hydroperoxide or hydrogen peroxide.

11. The process for producing an epoxy compound according to claim 7, wherein the olefin compound is a mono- or di-olefin compound having 2 to 60 carbon atoms.

12. The process for producing an epoxy compound according to claim 7, wherein the epoxy compound is an alkylene mono- or dioxide having 2 to 60 carbon atoms.

* * * * *